United States Patent [19]
Wanek et al.

[11] Patent Number: 6,121,362
[45] Date of Patent: Sep. 19, 2000

[54] SILICONE-BASED IMPRESSION MATERIAL

[75] Inventors: Erich Wanek, Kaufering; Joachim Zech, Hechendorf, both of Germany

[73] Assignee: ESPE Dental AG, Seefeld, Germany

[21] Appl. No.: 09/116,255

[22] Filed: Jul. 16, 1998

[30] Foreign Application Priority Data

Jul. 16, 1997 [DE] Germany .............. 197 30 515

[51] Int. Cl.$^7$ .................................. C08K 3/34
[52] U.S. Cl. .................. 524/448; 524/588; 523/109
[58] Field of Search .................... 524/588, 448; 523/109

[56] References Cited

U.S. PATENT DOCUMENTS 5,580,921  12/1996  Stepp et al. .................. 524/731

FOREIGN PATENT DOCUMENTS

| | | |
|---|---|---|
| 152887A2 | 8/1985 | European Pat. Off. . |
| 4031759A1 | 4/1992 | Germany . |
| 4129613A1 | 3/1993 | Germany . |
| 4323581A1 | 1/1995 | Germany . |
| 195 45 365A1 | 6/1997 | Germany . |
| 63-215770A2 | 9/1988 | Japan . |
| WO9317654 | 9/1993 | WIPO . |
| WO9632088 | 10/1996 | WIPO . |

Primary Examiner—Margaret G. Moore

[57] ABSTRACT

A monophase silicone impression composition which crosslinks by an addition reaction, includes the following components:

(a) organopolysiloxanes with at least two unsaturated groups in the molecule,
(b) organohydrogenpolysiloxanes with at least 2 SiH groups in the molecule,
(c) optionally, organopolysiloxane without reactive groups,
(d) a platinum catalyst,
(e) a hydrophilizing agent,
(f) diatomaceous earth,
(g) a filler, and
(h) optionally further customary additives, auxiliaries and dyestuffs, the amount of component (f) is 8 to 25 wt. %, based on the total weight of the cured composition, and the composition has a Shore hardness A to be determined in accordance with DIN 53505, of less than 45—measured after 30 minutes—, and a viscosity, determined in accordance with ISO 4823, of 31 to 39 mm. The impression composition is suitable for the production of provisional bridges and crowns. It replaces the alginate compositions used hitherto for this purpose and overcomes the disadvantages associated with these compositions.

14 Claims, No Drawings

SILICONE-BASED IMPRESSION MATERIAL

BACKGROUND OF THE INVENTION

1. Field of the Invention

The present invention relates to dental impression compositions based on silicones which crosslink by an addition reaction. The impression compositions according to the invention are distinguished by exhibiting a moderate viscosity, determined in accordance with ISO 4823, in the mixed state, good hydrophilicity and good flow capability simultaneously with outstanding stability. The recipes according to the invention are particularly suitable for mechanical mixing in automatic mixing apparatuses (e.g. Pentamix®, ESPE, Seefeld). The materials are employed as so-called monophase impression materials and, because of their flow properties and their ease of cutting, can be used in the practice as a substitute for alginates.

2. Description of the Conventional Art

In the dental practice, impression materials based on alginates are often employed for taking situation impressions of teeth and parts of the jaw for evaluation, diagnosis, planning and monitoring the accuracy of the fit of conservation, prosthetic and orthodontic work. In this procedure, the rough form of the jaw and teeth is recorded instantaneously by preparing a so-called situation impression. After the situation impression has been filled with gypsum suspension, the dentist then has the so-called study model, diagnostic model, documentation model or working and planning model. So-called counter-jaw models are also made to reproduce the opposite jaw for more extensive prosthetic work, and these are obtained by impressions with alginates.

An important field of use for alginate impression materials is the production of provisional crowns and bridges. In this procedure, a situation impression which records the starting situation is taken on the patient before the start of the preparation of one or more teeth. After the preparation has taken place, a provisional crown and bridge material, which is initially still in the pasty state, is incorporated at the appropriate points in the situation impression. This impression filled with the pasty material is then reset in the patient's mouth, where the crown and bridge material cures to form the provisional prosthesis. It is of particular importance here that the alginate material is easy to cut in the cured state, to influence shaping of the provisional prosthesis advantageously in favour of the stability by appropriate cutting of the alginate impression.

Alginates consist of derivatives of alginic acid which, after stirring with water, cure in a sol-gel process. The impressions are made as so-called one-phase or monophase impressions, i.e. only a single viscosity of the impression material is employed when taking the impression (see J. Wirz et al., "Abformung in der zahnärtzlichen Praxis [Impressions in the dental practice]", 1993, Gustav Fischer Verlag, p. 7). Some of the essential advantages of alginates for the fields of use described are:

high hydrophilicity
one-phase materials
good flow-on of the paste into undercuts
easy cutting of the cured impression
easy removal of the cured impression from the mouth
low costs.

Further advantages of alginate materials are
good ability to stand, i.e. no running of the paste off the impression spoon
short setting time, i.e. short residence time of the impression composition in the mouth.

However, the use of alginates is also associated with some decisive disadvantages:

no dimensional and storage stability of the cured impressions due to drying out. Because of this water loss and the resulting shrinkage, alginate impressions must be filled with gypsum suspension immediately after they are removed from the mouth.

no filling with gypsum several times is possible. Only one gypsum model can be produced from each impression. For example, it the model breaks, it is necessary to take the impression again.

disinfectability presents problems because of the tendency to absorb water and to swell.

in some instances incompatibility with gypsum, so that rough surfaces can occur on the gypsum model.

mixing as a rule is still done manually. Although some automatic mixing systems exist, they are of only minor importance, and furthermore also do not allow automatic metering into the spoon. As a result of the manual mixing, there are often air bubbles in the impressions, which lead to inaccuracies on the models.

Silicones which crosslink by an addition reaction represent another class of dental impression materials and are currently used as precision impression materials to produce extremely precise working models for production of dental prostheses. The properties of such compositions are described e.g. in the standards ISO 4823 and ADA 19. Silicones which crosslink by an addition reaction are described, for example, in U.S. Pat. No. 4,035,453. Since their curing takes place by a platinum-catalysed addition mechanism, which does not function on an aqueous basis, in principle they do not show the phenomenon of dimensional instability due to water loss. Furthermore, impressions made of silicones which crosslink by an addition reaction can be filled with gypsum suspension as often as desired, so that several models with a smooth gypsum surface can be cast with a single impression. The disinfectability of the impressions is also non-problematic with silicones which crosslink by an addition reaction.

Silicone impression compositions are entirely hydrophobic and show the problem that the recording sharpness of the impression is unsatisfactory due to poor flow-on properties of the paste as a result of inadequate hydrophilicity. These problems are described e.g. in DE-A-38 38 587, page 2, lines 19–23 or in EP-A-0 480 238, page 2, lines 1–26.

Various additives which increase the hydrophilicity of silicone impression compositions have been described in the literature to solve this problem. An overview of the prior art is to be found, for example in EP-A-0 480 238, page 2, lines 20–38. Additives which have proved to be particularly effective are polyether-siloxanes, such as are described, for example, in the international application WO 87/03001 or in EP-B-0 231 420. Further very effective additives are so-called polyether-carbosilanes, such as are described in WO 96/08230. Ethoxylated fatty alcohol derivatives, see e.g. EP-B-0 480 238, are also suitable for increasing the hydrophilicity and therefore for improving the flow-on properties. By employing these surfactants, the flow-on properties of the pastes are improved considerably, so that a good wettability can be achieved.

Commercially available silicone impression compositions which crosslink by an addition reaction are usually in a two-component form and comprise a so-called base paste and catalyst paste, in which the reactive components are separated from one another spatially for stability reasons. Curing of the materials takes place after the two pastes have been mixed in precisely defined volume ratios. Mixing is as a rule carried out manually or by pressing out of double-chamber cartridges, the pastes being conveyed through a mixing tube containing a static mixer, as a result of which intimate mixing of the pastes occurs. However, only relatively small amounts of paste can be mixed with this in a short time.

A further development of the handling properties of silicone impression compositions which crosslink by an addition reaction consists of the development of automatic mixing and metering systems for two-component impression compositions which have automatic conveying and mixing units, such as are described e.g. in U.S. Pat. Nos. 5,249,862, 5,286,105 and 5,332,122. The need for manual mixing of base pastes and catalyst pastes, above all when mixing larger quantities of material, is thus eliminated, since this can take place automatically and within a short time. The result is a completely homogeneous product which is free from bubbles (see the brochure ESPE Pentamix®, ESPE, Seefeld).

Silicones which crosslink by an addition reaction are chiefly used in a two-phase form: readily flowing or moderately flowing compositions are combined with poorly flowing or kneading compositions (see J. Wirz et al., p. 7).

There are indeed hydrophilic silicones which crosslink by an addition reaction and are employed in a monophase technique, i.e. are used in only a single viscosity. The use of such silicone impression compositions for the production of provisional bridges and crowns has not hitherto been thought of, since these materials are employed for taking precision impressions, which differs fundamentally from use for taking situation impressions. Commercially available hydrophilic monophase A silicones thus have quite a slow setting process, which as a rule is over 3 minutes for a setting time in the mouth (see J. Wirz, "Abformung in der zahnärztlichen Praxis [Impressions in the dental practice]", 1993, Gustav Fischer Verlag, p. 16 to 26). The setting time in the mouth is the time between positioning of the spoon with the impression material in the mouth of the patient and removal of the cured impression, and can also be called the mouth residence time or period. This is unfavourable for a situation impression material, since the dentist wants to save as much time as possible when working with this type of impression. Setting times of <3 minutes mouth residence time, preferably <2.5 minutes, and particularly preferably <2 minutes, are desirable properties for the dentist here. For example, the hydrophilic one-phase impression material "Imprint 2:5" (3M) has a setting time of 5 minutes, while a typical alginate impression material ("Alginoplast", Bayer) has a setting time of 1.5 minutes.

Furthermore, hydrophilic monophase A silicones are expensive impression compositions and as a rule have quite high hardnesses in the cured state, so that their Shore hardness A—measured in accordance with DIN 53505, 30 minutes after the start of mixing of the pastes—is as a rule I>50. Such impression compositions can therefore be separated from the objects of which the impression has been taken only with relative difficulty because of their hard nature. The crown and bridge material cured in the patient's mouth to give the provisional prosthesis is likewise difficult to separate from the impression material if this has too high a hardness. It could indeed be considered to modify the known hydrophilic monophase silicone impression materials by additives such that they are softer and more flexible in the cured state, so that they can then be separated easily from the objects of which the impression has been taken. An addition of plasticizers, such as e.g. commercially available plasticizers for plastics or silicone oils, also leads to a reduction in the costs. However, such plasticized silicone impression materials are then unacceptable in their ease of cutting. When producing the provisional crowns and bridges, the dentist must cut the cured impression at the interdental points, so that the material used for production of the provisional prostheses, which in itself is relatively brittle, does not become too thin at the interdental points and break. Experiments with hydrophilic monophase silicone impression materials which had merely been plasticized and had a Shore hardness A of less than 50 after curing could no longer be cut in the necessary way, since the interdental septa evade a scalpel elastically in the usual cutting technique.

SUMMARY OF THE INVENTION

The object of the invention is to provide an impression material which is suitable for the production of provisional bridges and crowns and indeed has the advantages but not the disadvantages of alginate impression materials.

In particular, the compositions should be suitable for automatic mixing in the Pentamix mixing apparatus. This means that it must be possible to establish a mixing ratio in a two-component presentation form of 5:1. The pastes must have an adequate ability to stand in the mixed state here, so that after introduction they do not drip out of the impression spoon into the patient's mouth. Nevertheless, the flow properties must be adequate, so that conveying and mixing in the Pentamix apparatus is possible in a suitable manner.

Surprisingly, in the context of the present invention, it has been found that this object can be achieved with silicone impression materials modified in a particular manner.

The invention thus provides a hydrophilic, monophase silicone impression material which crosslinks by an addition reaction and comprises the following components:

(a) organopolysiloxanes with at least two unsaturated groups in the molecule,
(b) organohydrogenpolysiloxanes with at least 2 SiH groups in the molecule,
(c) if appropriate organopolysiloxanes without reactive groups,
(d) platinum catalyst,
(e) hydrophilizing agent,
(f) diatomaceous earth,
(g) filler, and
(h) if appropriate further customary additives, auxiliaries and dyestuffs, the amount of component (f) being 8 to 25 wt. %, preferably 10 to 20%, based on the total weight of the cured rubber, and the composition having a Shore hardness A, to be determined in accordance with DIN 53505, of less than 45—measured 30 minutes after mixing of the pastes—preferably <40, and a viscosity, to be determined in accordance with ISO 4823, of 31 to 39 mm.

The compositions have a setting time in the mouth of <2.5 minutes, preferably <2 minutes, particularly preferably ≦1.5 minutes. The materials have a high hydrophilicity. The hydrophilicity can be determined by measuring the contact angle of a drop of water or a drop of saturated calcium sulphate solution to the surface of a cured specimen of the impression material. The measurement method is described, for example, in DE-A-43 06 997, page 5. The 3-minute value of the contact angle is preferably <60°, particularly preferably <50°, in particular <40°.

With a Shore hardness A of less than 45, the ease of removal of the cured impression from the mouth is to be described as very easy because of the flexibility of the rubber. Surprisingly, in spite of the flexibility of the material, a very good ease of cutting is achieved by the presence of component (f) in the amount ranges stated, so that the silicone impression composition can be used as an alginate substitute.

The possibility of using diatomaceous earth in hydrophilic silicones is described, for example, in EP-B-0 480 238, page 3, line 33, and in WO 93/04659, page 12. However, these publications contain no reference to the positive influence on the ease of cutting of silicones of low Shore hardness by the addition of diatomaceous earth within the amount ranges described.

Diorganopolysiloxanes with terminal triorganosiloxy groups, at least one of the three organic groups being a vinyl group, are preferred as component (a). Preferred diorganosiloxanes having this structure are represented by the following formula:

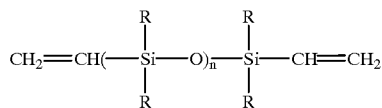

in which R represents an unsubstituted or substituted monovalent hydrocarbon group, which is preferably free from aliphatic multiple bonds, and n represents an integer. At least 50% of the radicals R are preferably methyl groups, and examples of other groups R are ethyl, vinyl and 3,3,3-trifluoropropyl groups. The value of n should be such that the polymer has a viscosity at 25° C. of between 200 and 200,000 mPa.s, preferably 1,000 to 10,000 mPa.s. Such molecules are described in U.S. Pat. No. 4,035,453, the disclosure of which is to be included herein to this extent. Components (a) are prepared by customary processes, which are described e.g. in W. Noll, "Chemie und Technologie der Silikone [Chemistry and technology of silicones]", Verlag Chemie Weinheim, 2nd edition 1964, page 162–206 or J. Burghardt, Chemie und Technologie der Polysiloxane [Chemistry and technology of polysiloxanes] in "Silikone, Chemie und Technologie [Silicones, chemistry and technology]", Vulkan Verlag, Essen, 1989, pages 23–37.

Linear polydimethylsiloxanes of the above structure with the stated viscosity ranges in which the end groups consist of dimethylvinylsiloxy units and the other substituents R in the chain consist of methyl groups are particularly preferred.

Component (b) is preferably an organopolysiloxane with at least 3 Si-bonded hydrogen atoms per molecule. This organopolysiloxane preferably contains from 0.01 to 1.7 wt. % silicon-bonded hydrogen. The silicone valencies which are not satisfied by hydrogen or oxygen atoms are satisfied by monovalent hydrocarbon radicals which are free from aliphatic multiple bonds. The hydrocarbon radicals can be substituted or unsubstituted. At least 50%, preferably 100%, of the hydrocarbon radicals bonded to silicon atoms consist of methyl radicals. Such components are also described in respect of structure and preparation in the abovementioned literature references.

The ratios of amounts of components (a) and (b) are preferably chosen such that 0.75 to 5 mol SiH units from component (b) are present per mol of unsaturated double bond of component (a). The sum of components (a) and component (b) is in the range from 10 to 40 wt. %, based on the total weight of all the components. It is preferably in the range from 15 to 25 wt. %.

Suitable components (c) are polymeric organosiloxanes without reactive substituents, such as are described e.g. in W. Noll, "Chemie und Technologie der Silikone [Chemistry and technology of silicones]", Verlag Chemie Weinheim, 1968, page 212 et seq. They are preferably linear, branched or cyclic organopolysiloxanes in which all the silicon atoms are surrounded by oxygen atoms or monovalent hydrocarbon radicals, it being possible for the hydrocarbon radicals to be substituted or unsubstituted. The hydrocarbon radicals can be methyl, ethyl, $C_2$–$C_{10}$-aliphatics, trifluoropropyl groups and aromatic $C_6$–$C_{12}$ substituents. Component (c) contributes towards dilution and expansion of the rubber network and acts as a plasticizer for the cured material. As a relatively favourable component, it also contributes towards reducing the production costs of the impression compositions according to the invention.

Polydimethylsiloxanes which contain trimethylsiloxy end groups are particularly preferred as component (c). The viscosity of component (c) is preferably in the range from 40 to 2,000 mPa.s, particularly preferably 50 to 1,000 mPa.s. The amount of component (c) is 0 to 40 wt. %, preferably 5 to 40 wt. %, particularly preferably 15 to 30 wt. %.

Component (d) is preferably a platinum complex which has been prepared from hexachloroplatinic acid by reduction with tetramethyldivinyldisiloxane. These compounds are known per se. Other platinum compounds which accelerate the crosslinking by an addition reaction are also suitable. Particularly suitable compounds are e.g. platinum-siloxane complexes such as are described e.g. in U.S. Pat. Nos. 3,715,334, 3,775,352 and 3,814,730. The platinum catalyst is preferably employed in amounts of 0.00005 to 0.05 wt. %, in particular 0.0002 to 0.04 wt. %, in each case calculated as elemental platinum and based on the total weight of the composition present with components (a) to (h). To control the reactivity, it may be necessary to have to add an inhibitor which prevents premature crosslinking to form the elastomer. Such inhibitors are known and are described e.g. in U.S. Pat. No. 3,933,880. Examples of these are acetylenically unsaturated alcohols, such as 3-methyl-1-butyn-3-ol, 1-ethynylcyclohexan-1-ol, 3,5-dimethyl-1-hexyn-3-ol and 3-methyl-1-pentyn-3-ol. Examples of inhibitors based on vinylsiloxanes are 1,1,3,3-tetramethyl-1,3-divinylsiloxane, and poly-, oligo- and disiloxanes containing vinyl groups.

Component (e) is an agent which imparts a hydrophilic nature or a hydrophilizing agent, which lowers the contact angle of a drop of water or an aqueous composition (e.g. gypsum suspension etc.) with respect to the silicone composition and therefore brings about a better wettability of the total composition in the moist medium of the mouth and hence better flow-on properties of the paste. Measurement of the contact angle for determination of the hydrophilicity of the impression compositions is described e.g. in DE-A-43 06 997, page 5, reference being made to this. The hydrophilizing agents preferably have no reactive groups, so that no incorporation into the polysiloxane network takes place. Suitable hydrophilizing agents are preferably wetting agents, which cannot be incorporated, from the group consisting of hydrophilic silicone oils which are described in WO 87/03001 and in EP-B-0 231 420, to the disclosure of which reference is to be made to this extent. The ethoxylated fatty alcohols described in EP-B-0 480 238 are furthermore preferred. Preferred hydrophilizing agents are moreover the polyether-carbosilanes known from WO 96/08230. The nonionic perfluoroalkylated surface-active substances described in WO 87/03001 are also preferred. The nonionic surface-active substances described in EP-B-0 268 347, i.e. the nonylphenol ethoxylates, polyethylene glycol mono- and diesters, sorbitan esters and polyethylene glycol mono- and diethers listed therein, are likewise preferred. The amounts of hydrophilizing agents employed are 0.1 to 10 wt. %, based on the total weight of all the components, preferably 0.2 to 2 wt. %, and particularly preferably 0.3 to 1 wt. %. The contact angle, measured after 3 min, of a drop of water on the surface of a cured material according to the invention is preferably less than 60°, particularly preferably <50°, in particular <40°.

Component (f) is called diatomaceous earth or kieselguhr. It comprises the very diversely shaped silicic acid skeletons of single-cell, microscopically small algae (diatoma) living in fresh or salt water. The materials are usually produced by surface mining and are also called infusorial earth, mountain flour or bacilli earth. The types of diatomaceous earth preferably employed are employed in calcined form. In this case, for example, drying is carried out in a rotary tube oven, with subsequent heating to approx. 700° C., organic constituents being burned. NaCl or ammonium chloride can also possibly be added here, undesirable iron being converted into volatile iron trichloride. The crude material can also be applied by other particular processes, e.g. with fluxes, such as $Na_2CO_3$, KOH or NaOH. Component (f) can also be in surface-modified, for example silanized, form. Suitable processes and agents are described in the description of component (g). The amounts employed are 8 to 25, preferably 10 to 20 wt. %, based on the total amount of the components. If the amount employed is below this, the ease of cutting of the cured elastomers according to the invention in the stated Shore hardness range of <45 (measured after 30 minutes after mixing the paste) is not improved to a sufficient extent. If the amounts employed are above this, instabilities occur in the pastes in the course of storage as a result of demixing effects. Preferred types of diatomaceous earth are e.g. the products with the trade names "Celatom" (marketed by e.g. Chemag), "Cellite 219", "Cellite 499", "Cellite 263 LD", "Cellite 281" and "Cellite 281 SS" from Johns-Manville, and "Diatomite 104", "Diatomite CA-3", "Diatomite IG-33", "Diatomite 143", "Diatomite SA-3" and "Diatomite 183" from Dicallite, and also the products "Clarcel" from Ceca.

The fillers according to component (g) which can be employed include non-reinforcing fillers having a BET surface area of up to 50 $m^2/g$, such as quartz, christobalite, calcium silicate, zirconium silicate, montmorillonites, such as bentonites, zeolites, including the molecular sieves, such as sodium aluminium silicate, metal oxide powders, such as aluminium oxides or zinc oxides or their mixed oxides, barium sulphate, calcium carbonate, gypsum and powders of glass and plastics. Possible fillers also include reinforcing fillers having a BET surface area of more than 50 $m^2/g$, such as e.g. pyrogenic or precipitated silicic acid and silicon/aluminium mixed oxides of high BET surface area. The fillers mentioned can be hydrophobized, for example by treatment with organosilanes or siloxanes or by etherification of hydroxyl groups to alkoxy groups. One type of filler or also a mixture of at least two fillers can be employed. The particle size distribution is preferably chosen such that no fillers with particle sizes >50 $\mu$m are present. The total content of fillers (g) is in the range from 10 to 80%, preferably 30 to 60%, the amounts of filler being chosen such that a Shore hardness A of the cured rubber of <45 after 30 minutes is not exceeded.

A combination of reinforcing and non-reinforcing fillers is particularly preferred. In this case, the reinforcing fillers are in amount ranges from 1 to 10 wt. %, in particular 2 to 5 wt. %. The non-reinforcing fillers form the difference to make up the total ranges mentioned, that is to say 9 to 70 wt. %, in particular 28 to 55 wt. %.

Preferred reinforcing fillers are pyrogenically prepared highly disperse silicic acids, which have preferably been hydrophobized by a surface treatment. The surface treatment can be carried out, for example, with dimethyldichlorosilane, hexamethyldisilazane, tetramethyl-cyclotetrasiloxane or polymethylsiloxanes. The surface areas of suitable pyrogenic silicic acids are preferably >50 $m^2/$, in particular 80 to 150 $m^2/g$. The presence of the surface-treated pyrogenic silicic acids contributes towards establishing the viscosity and improving the stability of the pastes. With amounts of <1 wt. %, as a rule no noticeable influence on the ability to stand is detectable, and amounts of >10 wt. % as a rule lead to a marked thickening of the pastes, so that adequate flow properties can no longer be obtained. During automatic mixing in the Pentamix apparatus, this leads to undesirable increases in temperature, which can lead to a rapid curing of the paste. Suitable products are described, for example, in the brochures from Degussa (Aerosil-Produkte [Aerosil products], Pigments [Pigments] publication series, no. 11, 5th edition, 1991, on page 79) and of Cabot Corp. (Cabosil-Produkte [Cabosil products], "CAB-O-SIL fumed silica in adhesives and sealants, Cabot, 1990).

Particularly preferred non-reinforcing fillers are quartzes, christobalites and sodium aluminium silicates, which can be surface-treated. The surface treatment can in principle be carried out by the same methods as described in the case of the reinforcing fillers.

The impression compositions according to the invention can furthermore comprise as component (h), if appropriate, additives such as plasticizers, pigments, antioxidants, release agents etc. They can likewise also comprise, for example, finely divided palladium or platinum as a hydrogen absorber. The metals can also be applied to support materials in this case. The compositions according to the invention comprise such additives in amounts of preferably 0 to 2 wt. %, particularly preferably 0.1 to 1 wt. %.

The compositions are prepared by mixing components (a) to (h), and cure in an addition reaction called hydrosilylation, in which the SiH groups of component (b) add on to the unsaturated groups of component (a) under the influence of the platinum catalyst (d). For storage stability reasons, it is preferable to formulate the compositions in a two-component presentation form, in which the entire component (b) is accommodated in a so-called base paste. Spatially separate from this, the entire component (d) is accommodated in a so-called catalyst past. Component (a) can be accommodated in either the catalyst paste or the base paste, preferably some of component (a) being accommodated in the base paste and some of component (a) being accommodated in the catalyst paste. The total amount of components (c), (e), (f), (g) and (h) can be accommodated in the catalyst paste or in the base paste, it being preferable for in each case some of the particular component to be accommodated in the catalyst paste and some in the base paste. It is particularly preferable for only the base paste to contain components (e) and (f).

The volume ratios of catalyst paste and base paste can be 10:1 to 1:10. Particularly preferred volume ratios of base paste: catalyst paste are 1:1 and 5:1 (5 parts of base paste : 1 part of catalyst paste). In the case of a volume ratio of 1:1, components (a) to (h) can be distributed over the base paste and catalyst paste as follows.

TABLE 1

| Component | Base paste | Catalyst paste | Total in base paste and catalyst paste |
|---|---|---|---|
| (a) | 10–48% | 10–48% | 14–24% |
| (b) | 2–10% | — | 1–5% |
| (c) | 0–60% | 0–60% | 15–30% |
| (d) | — | 0.0004–0.08% Pt | 0.0002–0.04% Pt |
| (e) | 0–4% | 0–4% | 0.2–2% |
| (f) | 0–40% | 0–40% | 10–20% |
| (g) reinforcing fillers | 0–10% | 0–10% | 2–5% |
| non-reinforcing fillers | 10–55% | 10–55% | 28–55% |
| (h) | 0–1% | 0–1% | 0.1–1% |

In the case of a volume ratio of 5 parts of base paste to 1 part of catalyst paste, preferred amounts can be represented as follows:

TABLE 2

| Component | Base paste | Catalyst paste | Total in base paste and catalyst paste |
|---|---|---|---|
| (a) | 2–29% | 0–50% | 14–24% |
| (b) | 1–6% | — | 1–5% |
| (c) | 0–36% | 0–30% | 15–30% |
| (d) | — | 0.002–0.2% Pt | 0.0002–0.04% Pt |
| (e) | 0–2.4% | 0–12% | 0.2–2% |
| (f) | 0–24% | 0–70% | 10–18% |
| (g) reinforcing fillers | 0–6% | 0–30% | 2–5% |
| non-reinforcing fillers | 10–60% | 10–70% | 28–55% |
| (h) | 0–1.2% | 0–1% | 0.1–1% |

At a volume ratio of 5:1, tubular film bags can be filled with the two pastes and the pastes can be mixed later with the aid of the PENTAMIX® (ESPE) mixing and metering apparatus shortly before use.

EXAMPLES

Reference Example 1

44.3 parts of a polydimethylsiloxane with terminal vinyl groups and a viscosity of 2,000 mPa.s at 23° C., 4.6 parts of a polydimethylsiloxane containing SiH groups and with a viscosity of 60 mPa.s at 33° C., 3.9 parts of a polydimethylsiloxane with a viscosity of 50 mPa.s at 23° C., 5.8 parts of a silanized pyrogenic silicic acid, 40.3 parts of silanized extra-fine quartz flour and 1.1 parts of the carbosilane surfactant hydrophilizing agent according to WO 96/08230, preparation example 2, are combined in a kneader by mixing to give a homogeneous base paste.

The catalyst paste is prepared by mixing 42.0 parts of a polydimethylsiloxane with terminal vinyl groups and a viscosity of 2,000 mPa.s at 23° C., 1.5 parts of a silanized pyrogenic silicic acid, 49.0 parts of sodium aluminium silicate filler, 7.0 parts of a solution of a complex of platinum and divinyltetramethyldisiloxane, comprising 1.3 wt. % platinum in a polydimethylsiloxane with terminal vinyl groups and a viscosity of 2,000 mPa.s at 23° C., and 0.5 part of coloured pigment.

50 g base paste and 10 g catalyst paste are mixed completely. After some minutes, a rubbery-elastic mass is obtained. 30 minutes after the preparation, the Shore hardness A is determined as 38. The viscosity of the mixed pastes is determined in accordance with ISO 4823 as 37 mm. 30 minutes after preparation, the contact angle after a wetting time of 3 minutes is determined as 20°.

The cured rubber comprises no diatomaceous earth and is difficult to cut with a scalpel. The setting time in the mouth is 3 minutes 15 seconds. Storage stability: After 4 weeks storage the pastes are unchanged.

Example 1

17.1 parts of a polydimethylsiloxane with terminal vinyl groups and a viscosity of 7,000 mPa.s at 23° C., 2.7 parts of a polydimethylsiloxane containing SiH groups and with a viscosity of 60 mPa.s at 23° C., 25.3 parts of a polydimethylsiloxane with a viscosity of 50 mPa.s at 23° C., 4.0 parts of a silanized pyrogenic silicic acid, 35.3 parts of silanized extra-fine quartz flour, 0.4 part of coloured pigment and 14.7 parts of diatomaceous earth (1 to 20 μm) and 0.5 part of the carbosilane surfactant hydrophilizing agent according to WO 96/08230, preparation example 2, are combined in a kneader by mixing to give a homogeneous base paste.

The catalyst paste is prepared by mixing 19.9 parts of a polydimethylsiloxane with terminal vinyl groups and a viscosity of 7,000 mPa.s at 23° C., 7.7 parts of a polydimethylsiloxane with a viscosity of 50 mPa.s at 23° C., 1.8 parts of a silanized pyrogenic silicic acid, 66.3 parts of sodium aluminium silicate filler, 0.02 part of coloured pigment and 4.3 parts of a solution of a complex of platinum and divinyltetramethyldisiloxane comprising 1.3 wt. % platinum in a polydimethylsiloxane with terminal vinyl groups and a viscosity of 2,000 mPa.s at 23° C.

50 g base paste and 10 g catalyst paste are mixed completely. After some minutes, a rubbery-elastic mass is obtained. The viscosity according to ISO 4823 is determined as 34 mm. The Shore hardness A after 30 minutes is 35. 30 minutes after preparation, the contact angle after a wetting time of 3 minutes is determined as 26°.

The cured rubber can be cut very easily with a scalpel. The setting time in the mouth is 1.5 minutes. Storage stability: After storage for 4 weeks the pastes are unchanged.

Comparison Example 1

39.8 parts of a polydimethylsiloxane with terminal vinyl groups and a viscosity of 7,000 mPa.s at 23° C., 11.9 parts of a polydimethylsiloxane containing SiH groups and with an approximate ratio of dimethylsiloxy:methylhydridosiloxy groups of 10:1, 3.0 parts of calcined kieselguhr, 5.0 parts of silanized pyrogenic silicic acid, 33.8 parts of silanized quartz, 1.5 parts of coloured pigment and 5.0 parts of a carbosilane surfactant hydrophilizing agent according WO 96/08230 are combined in a kneader by mixing to give a homogeneous base paste.

The catalyst paste is prepared by mixing 50.6 parts of a polydimethylsiloxane with terminal vinyl groups and a viscosity of 7,000 mPa.s at 23° C., 1.2 parts of a solution of a complex of platinum and divinyltetramethyldisiloxane with a platinum content of 1.3%, 3.6 parts of calcined kieselguhr, 2.0 parts of silanized pyrogenic silicic acid, 41.7 parts of a silanized quartz powder and 0.01 part of a coloured pigment with 1.0 part of a carbosilane surfactant hydrophilizing agent according to WO 96/08230, preparation example 2.

10 g base paste and 10 g catalyst paste are mixed completely. After some minutes, a rubbery-elastic mass is obtained. The viscosity according to ISO 4823 is determined as 36 mm. 30 minutes after preparation of the test specimen, the Shore hardness A is 36. 30 minutes after preparation, the contact angle after a wetting time of 3 minutes is determined as 20°.

The cured rubber is difficult to cut with a scalpel. The impression composition of this comparison example indeed comprises diatomaceous earth, but in too small an amount. Storage stability: After storage for 4 weeks, the pastes are unchanged.

Comparison Example 2

19.4 parts of a polydimethylsiloxane with terminal vinyl groups and a viscosity of 7,000 mPa.s at 23° C., 3.1 parts of a polydimethylsiloxane containing SiH groups and with a viscosity of 60 mPa.s at 23° C., 32.2 parts of a polydimethylsiloxane with a viscosity of 50 mPa.s at 23° C., 0.3 part of a silanized pyrogenic silicic acid, 44 parts of calcined kieselguhr (1 to 20 μm), 0.3 part of inorganic coloured pigment dispersed in 0.2 part of a polydimethylsiloxane with a viscosity of 50 mPa.s at 23° C. and 0.6 part of a carbosilane surfactant hydrophilizing agent according to WO 96/08230, preparation example 2, are combined in a kneader by mixing to give a homogeneous base paste.

The catalyst paste is prepared by mixing 42.0 parts of a polydimethylsiloxane with terminal vinyl groups and a viscosity of 7,000 mPa.s at 23°, 1.5 parts of a silanized pyrogenic silicic acid, 49.0 parts of sodium aluminium silicate, 7.0 parts of a solution of a complex of platinum and divinyltetramethyldisiloxane comprising 1.3 wt. % platinum in a polydimethylsiloxane with terminal vinyl groups and a viscosity of 2,000 mPa.s at 23° C., and 0.5 part of coloured pigment.

50 g base paste and 10 g catalyst paste are mixed completely. After some minutes, a rubbery-elastic mass is obtained. 30 minutes after preparation, the Shore hardness A is determined as 41. The viscosity of the mixed pastes is 32 mm in accordance with ISO 4823. 30 minutes after preparation, the contact angle after a wetting time of 3 minutes is 30°.

The cured rubber can be cut very easily with a scalpel. Storage stability: After storage for 3 days, the originally homogeneous paste separates into a liquid part comprising chiefly polysiloxanes and a solid part comprising chiefly filler. The paste can no longer be used in this state. The impression composition of this example indeed comprises diatomaceous earth, but in too large an amount. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. Monophase silicone impression composition which crosslinks by an addition reaction, comprising the following components:
    (a) an organopolysiloxane with at least two unsaturated groups in the molecule,
    (b) an organohydrogenpolysiloxane with at least 2 SiH groups in the molecule,
    (c) optionally, an organopolysiloxane without reactive groups,
    (d) a platinum catalyst,
    (e) a hydrophilizing agent having no reactive groups,
    (f) diatomaceous earth,
    (g) a filler, and
    (h) optionally, auxiliaries and dyestuffs, wherein the amount of component (f) is 8 to 25 wt. %, based on the total weight of the cured composition, and the composition has a Shore hardness A determined in accordance with DIN 53505, of less than 45 measured after 30 minutes, and a viscosity, determined in accordance with ISO 4823, of 31 to 39 mm.

2. Silicone impression composition according to claim 1, wherein the amount of component (f) is 10 to 18 wt. %.

3. Silicone impression composition according to claim 1, comprising:
    15–25 wt. % components (a)+(b),
    5–40 wt. % component (c),
    0.0002–0.04 wt. % component (d),
    0.2–2 wt. % component (e),
    10–18 wt. % component (f),
    30–60 wt. % component (g), and
    0.1–1 wt. % component (h).

4. Silicone impression composition according to claim 1, wherein the ratio of amounts of component (a) to component (b) is such that 0.75 mol to 5 mol SiH groups of component (b) are present per mol of unsaturated double bond of component (a).

5. Silicone impression composition according to claim 1, wherein component (f) is calcined diatomaceous earth.

6. Silicone impression composition according to claim 1, wherein component (g) is a reinforcing filler.

7. Silicone impression composition according to claim 6, wherein component (g) comprises pyrogenic silicic acid, which has optionally been hydrophobized by a surface treatment, as the reinforcing filler.

8. Silicone impression composition according to claim 1, wherein component (g) is a mixture of various fillers.

9. Silicone impression composition according to claim 8, wherein component (g) comprises a mixture of a reinforcing filler and a non-reinforcing filler.

10. Silicone impression composition according to claim 9, wherein component (g) comprises reinforcing fillers present in an amount of 1 to 10 wt. % and non-reinforcing fillers present in an amount of 9 to 70 wt. %, based on the weight of the total impression composition.

11. Silicone impression composition according to claim 10, wherein component (g) comprises reinforcing fillers present in an amount of 2 to 5 wt. % and non-reinforcing fillers present in an amount of 28 to 55 wt. %, based on the weight of the total impression composition.

12. Silicone impression composition according to claim 1, in the form of a base paste and a catalyst paste spatially separated therefrom, the entire component (b) being present in the base paste and the entire component (d) being present in the catalyst paste and the other components optionally being distributed over the two pastes.

13. Silicone impression composition according to claim 12, wherein the volume ratio of base paste to catalyst paste is 10:1 to 1:10.

14. Silicone impression composition according to claim 1, wherein the volume ratio of base paste to catalyst paste is 1:1 to 5:1.

* * * * *